United States Patent [19]

Satek

[11] Patent Number: 4,913,886
[45] Date of Patent: Apr. 3, 1990

[54] PRODUCTION OF IMPROVED COPPER ALUMINUM BORATE

[75] Inventor: Larry C. Satek, Wheaton, Ill.

[73] Assignee: Amoco Corporation, Chicago, Ill.

[21] Appl. No.: 361,278

[22] Filed: Jun. 5, 1989

[51] Int. Cl.$^4$ .................. C01B 35/00; C01B 35/10; C01B 15/12; C01B 35/12

[52] U.S. Cl. .................................. 423/277; 423/276; 423/277; 423/600; 502/202

[58] Field of Search ............... 423/276, 277, 600, 279; 502/202

[56] References Cited

U.S. PATENT DOCUMENTS 4,590,324  5/1986  Satek .................................. 585/444
4,755,497  7/1988  DeSimone et al. ................. 502/202

Primary Examiner—Robert L. Stoll
Assistant Examiner—Lori S. Freeman
Attorney, Agent, or Firm—Frederick S. Jerome; William H. Magidson; Ralph C. Medhurst

[57] ABSTRACT

A process is described for producing crystalline copper aluminum borate by forming an aqueous composition comprising a volatile organic liquid having at least partial miscibility with water, a source of copper(II) ions, a source of alumina, and a source of boria at a pH in range from about 4 to about 12 to form a homogeneous gel, drying the gel to form a superficially dry solid, and calcining the dry solid at a sufficiently high temperature to form crystalline copper aluminum borate. Also described is a method for producing a copper aluminum borate precursor which when dried and/or calcined to a sufficiently high temperature forms crystalline copper aluminum borate.

31 Claims, No Drawings

PRODUCTION OF IMPROVED COPPER ALUMINUM BORATE

BACKGROUND OF THE INVENTION

The present invention relates to a method for preparing improved copper aluminum borate catalyst More particularly, the invention involves producing copper aluminum borate by forming an aqueous composition comprising a volatile organic liquid having at least partial miscibility with water, a source of copper(II) ions, a source of alumina, and a source of boria at a pH in a range from about 4 to about 12, drying the composition to form a superficially dry solid, and calcining the dry solid at a sufficiently high temperature to form crystalline copper aluminum borate. Preferably, the process of producing copper aluminum borate comprises forming an aqueous composition comprising a source of copper-(II) ions, a source of alumina, and a source of boria, admixing with the aqueous composition a volatile organic liquid containing a chemical base to form a homogeneous gel, drying the gel to form a superficially dry solid, and calcining the dry solid at a sufficiently high temperature to form crystalline copper aluminum borate. The present invention is also directed to a method for producing a copper aluminum borate precursor which when dried and/or calcined to a sufficiently high temperature forms crystalline copper aluminum borate.

Catalytically active copper aluminum borate which is at least partially reducible with hydrogen under Temperature Programmed Reduction (TPR) at a temperature of no more than 350° C. and which has a surface area of at least 5 square meters per gram and a pore volume of at least 0.04 cc per gram is the subject of commonly assigned Satek U.S Pat. No. 4,590,324; of commonly assigned Kouba et al. U.S. Pat. No. 4,613,707; of commonly assigned Zletz et al. U.S Pat. No. 4,645,753; of commonly assigned Zletz U.S. Pat. No. 4,729,979; of commonly assigned De Simone et al. U.S Pat. No. 4,755,497; and of commonly assigned copending application of Zletz U.S. Ser. No. 285,103, filed Dec. 15, 1988. These applications disclose the preparation, characterization and utility of copper aluminum borate and are hereby incorporated by reference.

By way of general background, McArthur, in U.S. Pat. Nos. 3,856,702, 3,856,705 and 4,024,171, discloses that it has long been the practice in the art to impregnate or otherwise distribute active catalytic metals upon support materials having desired properties of porosity, surface area, thermal and mechanical stability, and suitably inert chemical properties. McArthur teaches that a superior catalyst support results from calcining certain aluminaboria composites within the temperature range of about 1,250° C.–2,600° F., which appears to produce a definite crystalline phase of $9\ Al_2O_3.2B_2O_3$ and also, in most cases, a crystalline phase of $2\ Al_2O_3.B_2O_3$, following which the aluminum borate support can be impregnated with solution(s) of desired catalytic salt or salts, preferably those that are thermally decomposable to give the corresponding metal oxides. Following impregnation, the finished catalysts are dried and, if desired, calcined at temperatures of, e.g., 500° to 1000° F. In the final catalyst, the active metal or metals may appear in the free form as oxides or sulfides or any other active form. Examples 1 to 6 of McArthur impregnate the calcined support with an aqueous solution of copper nitrate and cobalt nitrate to provide about 4% copper as CuO and 12% cobalt as $Co_2O_3$ in the final catalyst.

Addressing preparation of the aluminum-boria support, McArthur states that conventional compounding procedures may be employed in compositing the alumina and the boria. He explains that it is necessary to provide an intimate admixture of the finely divided materials such as may be achieved by grinding, mulling, or ball milling the dry powders together, following which the mixture is shaped into a porous, self-supporting aggregate, as by tableting, prilling, extruding, casting or other well-known techniques to form cylindrical pellets or extrudates, spheres or other granular forms. Nothing in McArthur discloses or suggests a method for preparing copper aluminum borate by forming an aqueous composition comprising a volatile organic liquid, a source of copper(II) ions, a source of alumina, and a source of boria, drying the composition to form a copper aluminum borate precursor which when calcined at a sufficiently high temperature produces crystalline copper aluminum borate, such being distinguishable from McArthur's catalyst preparation which involves initial formation of the calcined alumina-boria support followed by post-treatment with the active metal.

Uhlig discloses preparation of a green tetragonal solid copper aluminum borate having the structure $Cu_2Al_6B_4O_{17}$ in Diplomarbeit, Institute for Crystallography, Aacken (October 1976) "Phasen - und Mischkristall - Bildung im $B_2O_3$ - armeren Teil des Systems $Al_2O_3$-$CuO$-$B_2O_3$" ("Formation of Phases and Mixed Crystals in that Part of the $Al_2O_3$-$CuO$-$B_2O_3$ System With a Low $B_2O_3$ Content") which is hereby incorporated by reference, by grinding together solid boron oxide, copper oxide and alumina, sealing the ground metal oxides in a platinum tube and heating same at 1000° C. over the heating period of 48 hours. Attempts to produce this copper aluminum borate by the indicated route yield well-defined, dense crystalline particles which have an extremely low surface area and are accordingly not suitable for many catalysis processes due to the low porosity and surface area.

Asano, in U.S. Pat. No. 3,971,735, discloses a copper, zinc, aluminum and boron catalyst useful in low temperature methanol synthesis. The catalyst is preferably produced by forming a mixture of water-soluble salts of copper, zinc and boron, precipitating same with an alkali carbonate and mixing with alumina. The catalyst is then fired at approximately 300°–450° C.

Commonly assigned Satek U.S. Pat. No. 4,590,324 discloses preparation of catalytically active copper aluminum borate in a liquid medium which comprises (1) combining a source of divalent copper, trivalent aluminum and boron in the form of the oxide or borate, (2) drying the composition to remove water or diluent if necessary and (3) calcining the composition at a temperature sufficiently high to form crystalline copper aluminum borate having an X-ray diffraction pattern of $Cu_2Al_6B_4O_{17}$. Satek states that, while copper aluminum borate can be prepared by various techniques, it is generally preferred to combine the oxide precursor reagents in an aqueous medium and that the presence of volatile components in the preparation of copper aluminum borate, such as water, $NH_3$, acetate, etc., is advantageous in providing the copper aluminum borate with sufficient surface area and porosity for catalysis.

Recently, commonly assigned De Simone et al. U.S Pat. No. 4,755,497, disclosed a solid-state (i.e., dry)

preparation of copper aluminum borate in which a superficially dry mixture comprising alumina, boria, and the desired metal oxide are calcined to form crystalline copper aluminum borate. Further, De Simone et al. disclose that the solid reagents comprising precursors of copper aluminum borate should be ground to a powder, individually or as a combination, through a 0.25 mm screen in a high speed grinder and it is important that uniform particle sizes of all reagents be attained in order that the solid-state reaction to form crystalline copper aluminum borate proceeds as uniformly as possible upon calcination. In addition to problems in attaining uniform particle sizes of the several reagents, recent work has determined there is a number of blending and processing problems confronting preparation of catalyst by the solid-state process. First, blending of the oxide precursors is difficult to control. Also there is difficulty in achieving homogeneity of dry-mixed solid reagents which is important for reproducibility of catalytic properties. A further problem is in obtaining catalysts having high surface area at the calcination temperatures required to form crystalline copper aluminum borate from dry-mixed solid reagents.

Accordingly, there is a need for a reproducible aqueous-organic process for production of copper aluminum borate capable of producing high surface area catalysts. Before the present invention, the aqueous preparation of copper aluminum borate, generally described in Satek, was complicated by sensitivity of the thixotropic aqueous mixture or gel to agitation and a tendency of the mixture to undergo phase separation upon drying. Stability in the gel and homogeneity in the dry solids are believed to be important for catalyst reproducibility.

An additional need exists for a convenient method of preparing copper aluminum borate which results in a catalyst for chemical conversion of organic compounds, e.g., o-ethylaniline to indole, o-ethylphenol to benzofuran, p-cymene to p-methyl-alpha-methylstyrene, methane to chloromethanes, p-ethyltoluene to p-methylstyrene, cumene to p-methylstyrene, alpha-ethyl-naphthalene to acenaphthene, etc., which is susceptible to enhancement by doping with active metals.

Satek discloses that the optimum copper aluminum borate catalyst for dehydrogenating alkylaromatics will vary for each individual feed. Consistent with this, our recent work with the previously disclosed solid-state and aqueous prepared catalyst has encountered the problem that, where the catalyst is intended for use in dehydrogenation of p-cymene to p-methyl-alpha-methylstyrene and/or oxychlorinaton of methane with hydrochloric acid and oxygen, incorporation into the catalyst of active metals as a means of improving catalyst performance is accompanied by the unwanted side effect of lowering selectivity of the catalyst.

It is therefore a general object of the present invention to provide an improved method for preparing copper aluminum borate and, in particular, to provide an economical and reproducible aqueous-organic method for preparing a dry-solid precursor of crystalline copper aluminum borate such that the resulting catalyst is at least comparable to that produced according to techniques previously disclosed.

It is a further object of the invention to provide an improved method for preparing copper aluminum borate which results in a catalyst for conversion of methane to chloromethanes which can be markedly enhanced by incorporation of relatively small amounts of active metals. Other objects appear hereinafter.

Throughout the present specification and claims, the terms "miscibility of organic liquids with water," etc., are intended to denote a classification of organic liquids such that when about 5 mL of an organic liquid and about 5 mL of water are shaken together in a test tube for 1 minute, and then the mixture allowed to settle, no liquid-liquid interfacial meniscus is observed. The terms "partial miscibility of organic liquids with water," etc., are intended to denote a classification of organic liquids such that when about 5 mL of an organic liquid and about 5 mL of water are shaken together in a test tube for 1 minute, and then the mixture allowed to settle, a liquid-liquid interfacial meniscus is observed and the volume of the aqueous phase is larger than the volume of the organic phase. The terms "precursor," "copper aluminum borate precursor," "dry-solid precursor," etc., denote compositions which, upon calcination at a sufficiently high temperature, result in crystalline copper aluminum borate. The terms "chemical base," "base," etc., are intended to denote any substance which will accept a proton in the relevant aqueous/organic solvent.

In the discussion that follows, reference is made to Temperature Programmed Reduction. As discussed in Zletz copending U.S. Pat. No. 4,729,979 and Satek U.S. Pat. No. 4,590,324 (hereby incorporated by reference), this test was carried out by placing $1.5 \times 10^{-4}$ moles of copper aluminum borate in a 0.6 mm outside diameter vycor tube heated by an electric furnace. The tube was purged with helium or argon by heating to 300° C. After cooling to ambient temperature, the gas feed to the vycor tube was switched to either 5% carbon monoxide in helium or 5% hydrogen in argon and the temperature was ramped to about 850° C. at 8° C./min. The temperature was controlled and ramped by a programmer equipped with a temperature controller. The change in gas composition of the effluent was detected with a thermal conductivity cell equipped with output to a strip-chart recorder. The carbon dioxide formed was removed from the effluent by a bed of ascarite and the water formed was removed by magnesium perchlorate. Unless otherwise stated, pore volume, surface area and average pore radius was determined by BET nitrogen adsorption (desorption test).

SUMMARY OF THE INVENTION

The objects of this invention are provided for in a method for producing copper aluminum borate which comprises forming an aqueous composition comprising a volatile organic liquid having at least partial miscibility with water, a source of copper(II) ions, a source of alumina, and a source of boria at a pH in a range from about 4 to about 12, drying the composition to form a superficially dry solid, and calcining the dry solid at a sufficiently high temperature to form crystalline copper aluminum borate.

In one aspect, the invention describes the process of producing copper aluminum borate comprises forming an aqueous composition comprising a source of copper-(II) ions, a source of alumina, and a source of boria, admixing with the aqueous composition a volatile organic liquid containing a chemical base to form a homogeneous gel, drying the gel to form a superficially dry solid, and calcining the dry solid at a sufficiently high temperature to form crystalline copper aluminum borate.

In another aspect, the invention describes a method for producing a copper aluminum borate precursor which comprises forming an aqueous composition comprising a volatile organic liquid having at least partial miscibility with water, a source of copper(II) ions, a source of alumina, and a source of boria, preferably, at a pH in a range from about 6 to about 10, to form a homogeneous gel which when dried to a superficially dry solid and/or calcined at a sufficiently high temperature forms crystalline copper aluminum borate.

Among the advantages offered by the present invention is that it eliminates the need to grind solid reagents to uniform size and blend dry solids to obtain a homogeneous mixture in the preparation of copper aluminum borate precursor, thus greatly simplifying the overall preparation of the catalyst. The aqueous-organic method also enhances the consistency (i.e., reproducibility) of the catalyst and enables the catalyst to be improved by incorporation of active metals using a sol or solution in the aqueous-organic mixture. Because the crystalline copper aluminum borate is formed at lower temperatures during calcination, porosity and surface area can be controlled to predetermined levels, even up to surface areas of about 200 m²/g and higher.

DETAILED DESCRIPTION OF THE INVENTION

In the process of the present invention for producing copper aluminum borate, a homogeneous gel is formed of an aqueous-organic medium comprising a volatile organic liquid having at least partial miscibility with water. Volatile organic compounds useful in the present invention typically have normal boiling points in a temperature range downward from about 140° C. Suitable organic compounds include alcohols, ethers, aldehydes and ketones having from about 1 to about 5 carbon atoms per molecule, such as methanol, ethanol, 2-propanol, 2-butanol, 2-methyl-2-propanol, 2-propen-1-ol, methoxymethane, methoxyethane, 1-methoxypropane, 2-methoxypropane 2-ethoxypropane, 1,3-dioxane, 1,4-dioxane, propanone, butanone, 3-pentanone, and 2-pentanone, and N,N-dimethylformamide. Of these organic compounds methanol, ethanol, and N,N-dimethylformamide are preferred.

Advantageously, in the process of the present invention, the amounts of water and volatile organic liquid used are the least amounts needed to consistently obtain a homogeneous copper aluminum borate precursor. Likewise, suitable ratios of organic liquid to water for each liquid system are best determined experimentally. Typically, the ratios of organic liquid to water by volume are less than about 1, preferably in a range from about 0.01 to about 0.99, more preferably in a range from about 0.1 to about 0.9.

In somewhat greater detail, the method for producing a copper aluminum borate precursor comprises forming an aqueous composition comprising a source of copper(II) ions, a source of alumina, and a source of boria, admixing with the aqueous composition a volatile organic liquid containing a chemical base to form a homogeneous gel which, when dried to form a superficially dry solid and/or calcined to a sufficiently high temperature, forms crystalline copper aluminum borate.

Suitable sources of copper for use in this invention can be a sol or any reasonably soluble salt of copper(II) ions, or precursor thereof which is at least partially soluble in the dispersing liquid, such as the acetate, formate, nitrate, carbonate, chloride, bromide, sulfate and the like. Salts of copper(II) such as copper(II) nitrate, copper(II) acetate, and copper(II) carbonate, etc. are preferred. Copper nitrate is preferred as it behaves well in air drying. When the source of copper(II) is a sol, oxides are preferred.

Typically, best results are obtained when each of the sources used is chosen to reduce the content of foreign anions and cations in the reaction mix.

The source of alumina is any material capable of producing alumina, such as aluminum nitrate, aluminum acetate, aluminum borate, etc., but preferred is a well dispersed, liquid source such as an alumina sol.

The source of boria is a material such as borate or boric acid with pure boric acid being preferred.

Generally, these components can be combined in an aqueous or aqueous-organic medium in approximately stoichiometric proportions sufficient to provide copper aluminum borate having the mixed metal oxide formula $2CuO \cdot 3Al_2O_3 \cdot 2B_2O_3$ or the empirical formula $Cu_2Al_6B_4O_{17}$.

Typically, the mole ratios of the various reactants can be varied to produce the copper aluminum borate by the method of this invention. Specifically, the mole ratios in terms of oxides of the initial reactant concentrations are characterized by the general mixed oxide formula

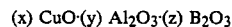

$$(x) \; CuO \cdot (y) \; Al_2O_3 \cdot (z) \; B_2O_3$$

where x, y and z are numbers representing molar amounts of the oxides of the source reagents.

The mole ratios of $CuO/B_2O_3$, calculated as x/z, are about 0.1 to about 10, preferably about 0.15 to about 0.6, and most preferably about 0.25 to about 4, and the mole ratios of $Al_2O_3/B_2O_3$, calculated as y/z, are from about 0.1 to about 10, preferably about 0.15 to about 6, and more preferably about 0.25 to about 4.

In somewhat greater detail, a preferred procedure is to dissolve the boria source and disperse the alumina source in water or water and a volatile organic liquid with mixing in a blender for about 3–5 minutes, then add an aqueous sol or solution of a source of copper(II) to the blender followed by gelation by admixing with the aqueous mixture a volatile organic liquid, preferably methanol, ethanol, or N,N-dimethylformamide, containing a chemical base.

Suitable basic compounds include oxides, hydroxides and salts of alkali metal elements, ammonium hydroxide, and hydroxides of organic cations, such as methylammonium hydroxide or tetramethylammonium hydroxide. Preferred chemical bases comprise at least one quaternary ammonium cation selected from the group consisting of tetramethylammonium, tetraethylammonium, benzyltrimethylammonium, trimethyl-n-octylammonium, dibenzyldimethylammonium, and cetyltrimethylammonium. The presence of the ammonia as well as other volatile components in the gelled mixture, such as acetate ion, nitrate ion, etc., is advantageous in providing the final calcined solid with sufficiently high surface area and porosity desirable for catalytic reactions.

Typically, the pH of the aqueous mixture is in a range from about 4 to about 12. If the reaction media is too acid or too basic, the desired solid generally will not form or other contaminating phases are formed in addition to the desired product. To some extent the pH of the reaction mixture controls surface properties of the final calcined solid material. Preferably, the pH of the reaction mixture is in a range from abut 6 to about 10, more preferably about 7 to about 9, in order to gel the reaction mixture.

If desired, non-volatile cations such as alkali metal or alkaline earth metal cations can be present during the preparation of the copper aluminum borate precursor. Suitable alkali metal and alkaline earth metal compounds include the oxides, hydroxides and salts of lithium, sodium, potassium, rubidium, cesium, magnesium, calcium, strontium, and barium, such as lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. Of these, potassium, in the form of the oxide or in a form readily convertible to the oxide, is preferred. The aluminum borate can be treated with from about 0.05 to 50 wt. % dopant based on the weight of the aluminum borate. The alkali metal or alkaline earth metal compound can be dry blended with the aluminum borate; dissolved in a suitable solvent, preferably water, mixed with the aluminum borate and dried; or aqueous solutions of same can be added to feedstocks going to a reactor containing the aluminum borate catalyst.

The gelled mixture is mildly dried for anywhere from a few hours to a few days at varying temperatures, typically about 20° to about 225° C., to form a superficially dry cake which is a copper aluminum borate precursor. Advantageously, the gelled mixture is allowed to air-dry, usually for about 1-3 days, followed by vacuum drying, typically at a pressure of about 0.3 atmosphere for about 15 to 25 hours at about 100° C. to 150° C. with a purge of dry gas, such as nitrogen.

The superficially dry precursor is calcined, preferably at a temperature within the range of about 650° to about 1000° C. for a reaction time that is sufficient to effect formation of crystalline copper aluminum borate, typically a reaction time within the range of about 2 to about 30 hr. Samples of material can be removed during calcination to check the degree of crystallization and determine the optimum calcination time.

The crystalline material formed can be crushed to a powder or to small particles and extruded, pelletized, or made into other forms suitable for its intended use. In a preferred embodiment of the above-described method, the crystalline material formed can be washed with a solvent, preferably an aqueous solvent, which removes impurities such as excess boria, without destroying the crystalline material formed, mildly dried for anywhere from a few hours to a few days at varying temperatures, typically about 50° to about 225° C., to form a dry cake which can then be treated as required for its intended use.

The solid materials made by this invention can be admixed with or incorporated within various binders or matrix materials depending upon the intended process use. They are combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, Sterotex (a powdered vegetable stearine produced by Capital City Products, Co., Columbus, Ohio), or other binders well known in the art.

Advantageously, a crystalline material formed according to this invention is formed or combined with from about 0.05 to about 50 wt % of at least one compound of a metallo element selected from the group consisting of Groups IA, IIA, IIB, VIB and VIII of the Periodic Table based on the weight of crystalline material.

Suitable alkali metal (Group IA), alkaline earth metal (Group IIA), low melting metal (Group IIB) brittle metal (Group VIB), and heavy metal (Group VIII) compounds include the oxides, hydroxides and salts of lithium, sodium, potassium, rubidium, cesium, magnesium, calcium, strontium, barium, chromium, zinc, cadmium, lanthanum, cerium, and thorium, such as lithium hydroxide, sodium hydroxide, potassium hydroxide, magnesium hydroxide, potassium oxide, sodium oxide, potassium carbonate, sodium carbonate, sodium bicarbonate, potassium nitrate, potassium borate, sodium borate, potassium chloride, potassium acetate, sodium propionate, potassium maleate, etc. Of these, potassium and chromium, in the form of the oxide or in a form readily convertible to the oxide, are preferred. The solid materials formed according to this invention can be treated with from about 0.05 to 50 wt % dopant based on the weight of the solid material. The metallo compound or compounds can be dry-blended with the aluminum borate, dissolved in a suitable solvent, preferably water, mixed with the solid material and dried; or aqueous solutions of same can be added to feedstocks going to a reactor containing the solid material catalyst.

Particularly useful is the fact that when these solid catalyst compositions are used in liquid and/or gas phase processes, the products of chemical conversion are easily separated from the solid catalyst material. Also useful is the fact that when these solid catalyst compositions are used in such fluid-phase processes, the active metallo element components are only slowly extracted, leading to longer catalyst lifetime.

Preferably, where the catalyst is to be used for the dehydrogenation catalyst, density is desirably in the range of from about 0.48 g/ml to about 1.1 g/ml, and preferably in the range of about 0.5 /g/ml to about 0.8 g/ml.

After the copper aluminum borate precursor has been dried, calcination of the precursor is carried out at a temperature in the range of from about 650° to about 1000° C., preferably at least about 700° C. if the catalyst is to be used for syngas conversion (as disclosed in commonly assigned co-pending Zletz U.S. Ser. No. 285,103), and at least about 800° C. if the catalyst is to be used for dehydrogenation (as disclosed in Satek U.S. Pat. 4,590,324), for about 0.1 to 24 hours, typically in air. The higher the calcination temperature the shorter the calcination time. Calcinations below about 800° C. tend to provide a catalyst that is more active in oxychlorination of methane. Calcinations above about 800° C. tend to provide a green crystalline material that is more active in dehydrogenation reactions than the green crystalline material obtained below about 800° C. Other things being equal, the higher the calcination temperature, the lower the surface area and porosity of the copper aluminum borate. In the present invention, the superficially dry copper aluminum borate precursor mixture is calcined to a temperature in a range from about 650° to about 900° C., typically for 3-24 hours, preferably to a temperature between 650° and 860° C. for about 8 to about 20 hours. I have found a preferred calcining temperature to be in a range from about 680° C. to about 840° C.

When copper aluminum borate is used as a catalyst in the dehydrogenation of organic compounds or in a reaction medium containing a reducing gas, at least part of the copper in the copper aluminum borate is converted into finely divided copper on an aluminum borate support. In some reactions, such as in the dehydrogenation of alkylaromatics to alkenylaromatics, substantially all of the copper in the still active catalyst can be present as finely divided copper metal on an aluminum borate support, i.e., in the aluminum borate matrix. In other cases, the active catalyst always contains some copper aluminum borate. If part of the copper in copper aluminum borate is replaced with another divalent metal, for example zinc or nickel, copper in the compound is still reducible to metallic copper at relatively low temperature.

If neat copper aluminum borate having the empirical formula $Cu_2Al_6B_4O_{17}$ is viewed as having the structure $3Al_2O_3 \cdot 2CuO \cdot 2B_2O_3$, the reduction with CO or $H_2$ can be represented in its simplest terms as follows:

$3Al_2O_3 \cdot 2CuO \cdot 2B_2O_3 + 2H_2 \longrightarrow$ $3Al_2O_3 \cdot 2B_2O_3 + 2\,Cu + 2H_2O$ $3Al_2O_3 \cdot 2CuO \cdot 2B_2O_3 + 2CO \longrightarrow$ $3Al_2O_3 \cdot 2B_2O_3 + 2\,Cu + 2CO_2$ X-ray diffraction patterns of the products indicate that the aluminum borate crystal has the formula $2Al_2O_3 \cdot B_2O_3$ and that part of the $B_2O_3$ in the original copper aluminum borate crystal has been driven off and/or is present in the amorphous state. Partial replacement of the copper in copper aluminum borate with other divalent metals does not appear to interfere with the reduction of the copper to zero valent copper.

Unreduced copper aluminum borates (CuAB) have a distinguishing crystalline structure while substantially fully reduced CuAB (Cu on AB) has a different related crystalline structure as evidenced by the significant lines of their X-ray diffraction patterns. The 5.29 line has arbitrarily been set at 100 for Cu on AB in order to facilitate a comparison with ASTM data for such materials as CuAB and aluminum borate. The X-ray diffraction patterns in Table A show the significant lines for substantially fully reduced CuAB (copper on aluminum borate) of this invention, unreduced CuAB of this invention, CuAB of Uhlig, $Al_4B_2O_9$ and copper.

X-ray data were determined by standard techniques. The radiation was the K-alpha doublet of copper, and a proportional counter spectrometer with a strip chart pen recorder was used. The peak heights, I, and the positions as a function of 2 times theta, where theta is the Bragg angle, were read from the spectrometer chart. From these the relative intensities, 100 $I/I_0$, where $I_0$ is the intensity of the strongest line or peak, and d (obs.), the interplanar spacing in Angstroms, corresponding to the recorded lines, were calculated. In Table A, the relative intensities are given in terms of the symbols VVS=very very strong (>100), VS=very strong (80-100), S=strong (50-80), M=Medium (20-50), W=weak (10-20) and VW=very weak (<10).

TABLE A

| (d)Angstroms | Cu on AB | CuAB | Uhlig CuAB | $Al_4B_2O_9$ | Cu |
|---|---|---|---|---|---|
| 7.50 ± .1 | | VW-M | M | | |
| 5.29 ± .05 | VS | VS | VS | VS | |
| 5.00 ± .05 | | S | S | | |
| 4.92 ± .03 | W-M | | | W | |
| 3.73 ± .03 | | W-M | W | | |
| 3.64 ± .03 | | VW-W | VW | | |
| 3.58 ± .03 | VW-M | | | VW | |
| 3.35 ± .03 | VW-M | W | W | M | |
| 2.98 ± .03 | | VW-W | W | | |
| 2.84 ± .03 | | VW-W | VW | | |
| 2.78 ± .02 | VW | | | | |
| 2.64 ± .02 | M | M-S | M | M | |
| 2.61 ± .02 | | W-M | W | | |
| 2.50 ± .02 | | W-M | VW | | |
| 2.45 ± .02 | W-M | | | W | |
| 2.26 ± .02 | | W-M | W | | |
| 2.22 ± .02 | W | | | VW | |
| 2.16 ± .02 | | M | W | | |
| 2.13 ± .02 | M | | | W-M | |
| 2.07 ± .02 | VVS | M | M | W | S |
| 1.97 ± .02 | VW-W | M | W-M | | |
| 1.91 ± .02 | VW | | VW | VW | |
| 1.86 ± .01 | | W-M | VW | | |
| 1.81 ± .01 | VVS | M | W | | M |
| 1.76 ± .01 | | VW | VW | | |
| 1.67 ± .01 | W | W-M | W | | |
| 1.60 ± .01 | | W-VW | VW | | |
| 1.555 ± .01 | W | W-VW | VW | W | |

As indicated above, the substantially fully reduced copper aluminum borate X-ray diffraction lines correspond primarily to the X-ray diffraction lines of the $Al_4B_2O_9$ and copper.

The significant X-ray diffraction lines for copper aluminum borate are set forth below in Table B.

TABLE B

| (d)Angstroms | Strength |
|---|---|
| 5.29 ± .05 | VS |
| 5.00 ± .05 | S |
| 3.73 ± .03 | W-M |
| 2.64 ± .03 | M-S |
| 2.61 ± .02 | W-M |
| 2.50 ± .02 | W-M |
| 2.26 ± .02 | W-M |
| 2.16 ± .02 | M |
| 2.07 ± .02 | M |
| 1.97 ± .02 | M |
| 1.86 ± .01 | W-M |
| 1.81 ± .01 | M |

Copper aluminum borate prepared according to the present invention can be used for oxidation, dehydrogenation, conversion of syngas, hydrogenation, etc., as described in commonly assigned Satek U.S. Pat. No. 4,590,324; Kouba et al. U.S. Pat. No. 4,613,707; Zletz et al. U.S. Pat. No. 4,645,753; Zletz U.S. Pat. No. 4,729,979; De Simone et al. U.S. Pat. No. 4,755,497; and of commonly assigned copending application of Zletz U.S. Ser. No. 285,103, filed Dec. 15, 1988.

EXAMPLE 1

This example illustrates the homogeneity and high BET surface area of material prepared according to the aqueous/organic method of the present invention. Copper nitrate hydrate (58.13 g, 0.25 mol), alumina sol (587.2 g of an 6.52% $Al_2O_3$ sol, 0.38 mol) and boric acid (30.8 g, 0.50 mol) dissolved in 150 mL warm deionized water were added to a small Waring blender, and mixed for about 2 minutes at a low speed. A total of 560 mL of a 20% ammonium hydroxide in methanol solution was added in several portions, with mixing, to gel the material which had a final pH of 9 and was spread onto 35×45 cm trays for air drying. After several days, the sample is placed in a vacuum oven at 120° C. and 0.3 atm pressure for 24 hours. A portion of the solids, 40.13 g, was calcined according to the following program:

$$25° C. \xrightarrow{4 \text{ hrs}} 175° C. \xrightarrow{12 \text{ hrs}} 400° C. \xrightarrow{2 \text{ hrs}}$$

$$700° C. \xrightarrow{4 \text{ hrs}} 700° C. \xrightarrow{2 \text{ hrs}} 120° C. \longrightarrow RT$$

The BET surface area of the resulting material, identified as Example 1, measured 203 m²/g X-ray powder diffraction analysis of the material showed a pattern of low crystallinity comprising significant lines substantially as described in Table B for copper aluminum borate. Analytical electron microscopy of a number of particles prepared as a water dispersion on carbon coated nickel grid showed that individual particles analyze as copper aluminum borate. Furthermore, element mapping of particles showed complete homogeneity down to at least 300–500 pm.

EXAMPLE 2

This example illustrates preparation of copper aluminum borate catalyst according to the aqueous/organic method of the present invention. Copper nitrate hydrate (232.2 g, 1.00 mol) dissolved in 200 mL deionized water was placed into a one gallon Waring blender with 1725.8 g of alumina sol (8.88% Al$_2$O$_3$, 1.50 mol of Al$_2$O$_3$). Boric acid (122.9 g, 2.00 mol) dissolved in 600 mL warm deionized water was added to the blender. The mixture was blended for 2 minutes at a low speed. The material was light blue and had a pH of 3.8. A total of 500 mL of a 20% tetramethylammonium hydroxide in methanol solution was added in several portions, with mixing, to gel the material which was spread onto 35×45 cm trays for air drying. After several days, the sample is placed in a vacuum oven at 120° C. and 0.3 atm pressure for 24 hours. A portion of the solids, 40.13 g, was calcined according to the following program:

$$120° C. \xrightarrow{2 \text{ hrs}} 250° C. \xrightarrow{4 \text{ hrs}} 830° C. \xrightarrow{8 \text{ hrs}}$$

$$830° C. \xrightarrow{2 \text{ hrs}} 250° C. \longrightarrow RT$$

The resulting material (20.3 g) was doped with potassium using potassium carbonate, 2.03 g, dissolved in 5 mL deionized water. The sample was treated with the potassium carbonate solution and subsequent beaker washings until the point of incipient wetness. The wet solids were air dried and calcined to 600° C. for 6 hours. ICP analysis showed 18.7% copper, 25.7% aluminum, 6.8% boron. The material, identified as Example 1, exhibited an x-ray powder diffraction pattern comprising significant lines substantially as described in Table B for copper aluminum borate.

COMPARATIVE EXAMPLE A

Copper aluminum borate, identified as Example A, was prepared according to the method of Example 2, except that ammonium hydroxide in aqueous solution was used to adjust pH in place of the tetramethylammonium hydroxide in methanol solution. The ICP analysis of this material was 20.9% copper, 25.3%, aluminum, 6.7% boron.

EXAMPLE 3

This example illustrates a comparison of the resulting catalysts of Example 2 and Example A for catalytic dehydrogenation. Testing for dehydrogenation activity was carried out on a continuous operating unit using the conversion of p-cymene to p-methyl-alpha-methylstyrene as a reference reaction. An 18 cc sample of the catalyst (about 12–13 g) sized to 18–24 mesh was used. The p-cymene was fed at 6 cc/hr (0.33 hr$^{-1}$ LHSV, 0.4–0.5$^{-1}$ WHSV) and steam was added at a 6:1 (water::organic) weight ratio. The operating temperature was 593° C. Samples were taken daily for a period of 10 days, and analyzed with a gas chromatograph equipped with a FID detector. Conversions and selectivities were reported in area percents. Routinely obtained material balances typically showed better than a 97% recovery.

Example 2 catalyst obtained a conversion of 40% with a 95% selectivity to p-methyl-alpha-methylstyrene. In contrast, under identical conditions, Example A catalyst obtained only a conversion of 28% with a 90% selectivity to p-methyl-alpha-methylstyrene.

EXAMPLE 4

Copper nitrate hydrate (232.8 g, 1.00 mol) in 200 mL deionized water, alumina sol (1653.2 g of a 9.26% Al$_2$O$_3$, 1.50 mol) and boric acid (123.9 g, 2.00 mol) dissolved in warm deionized water were added to a 1 gal Waring blender, with mixing. A total of 800 mL of 20% tetramethylammonium hydroxide was added to the mixture, in portions with mixing, to obtain a gel having a final pH of 5.7. The gel was spread onto trays for drying and vacuum dried at 120° C. in a nitrogen purge, at 0.3 atm. overnight. A portion, 150 g, was placed in a calcining oven and calcined by the following program:

$$120° C. \xrightarrow{2 \text{ hrs}} 250° C. \xrightarrow{4 \text{ hrs}} 770° C. \xrightarrow{8 \text{ hrs}}$$

$$770° C. \xrightarrow{2 \text{ hrs}} 250° C. \xrightarrow{1 \text{ hr}} 120° C. \longrightarrow RT$$

The material, 79 g, was removed from the oven and identified as Example 4.

COMPARATIVE EXAMPLE B

This example illustrates preparation of copper aluminum borate from a dry-prepared precursor according to De Simone et al. U.S. Pat. No. 4,755,497. Copper acetate, Cu(OAc)$_2$-H$_2$O (40.4 g), boric acid (25 g) and Amalo No. 15 alumina (77.5% Al$_2$O$_3$, 40.0 g) were hand mixed in a jar for 1 min. and then ground thoroughly through a 0.25 mm screen in a high speed grinder to assure that all reagents were ground to a similar particle size for uniform mixing. The ground reagents were then dry-mixed with 5 wt. % finely ground Sterotex. Roller mixing of the Sterotex and the ground reagents was carried out for about 30 minutes. The resulting liquid free precursor mixture was then formed into ⅛ in diameter by 3/16 in length pellets using a Stokes Model 521-2 four ton single punch powder compacting press. Crush strength of the pellets was maintained between 4.5 and 6 pounds to monitor crush strength of the pellets. The pelletized precursor was then calcined using the following calcination program:

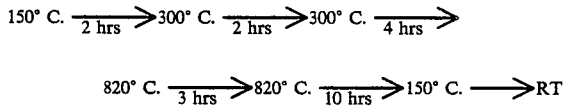

The resulting material was identified as Example B.

EXAMPLE 5

This example illustrates a comparison of the resulting catalysts of Example 4 and Example B for catalytic dehydrogenation. Testing for dehydrogenation activity was carried out on a continuous operating unit using the conversion of o-ethyl aniline to indole.

The reactions were carried out in a gas phase flow-through fixed-bed reactor. Reactors were ⅜ in O.D. by 21 in quartz tubes fitted with a ¼ in thermowell; catalyst frit was located approximately 1 in below center. This allowed the catalyst to be loaded in such a was as to minimize empty reactor space in the hottest reactor zones. Heat was provided by a single zone Lindberg furnace regulated by Harvard syringe pumps. Gaseous reactants were regulated with micrometering valves, measured by gas bubble meters. Liquid products were collected in a series of traps employing water/ice, dry ice/acetone, and a water cooled spiral condenser; gaseous products were not collected. Reactants and products were identified and quantified by gas chromatographic analysis on a Hewlett Packard 5790 fitted with an OV 225 6 gtx ¼ in packed glass column. Product identities were determined and confirmed by comparison with authentic samples and by GC/mass spectroscopy analysis. Response factors were determined for o-ethylaniline, indole and indolene. Product concentrations have been calculated from area percent data. Resulting data are shown below in Table I and Table II.

TABLE I o-Ethylaniline to Indole[1]

| WHSV hr$^{-1}$ | Conversion mole % | Selectivity Indene- mole % | Selectivity Indolene mole % |
|---|---|---|---|
| Example 4 (Aqueous-Organic) | | | |
| 0.12 | 93 | 91 | — |
| 0.18 | 94 | 86 | 3 |
| 0.24 | 93 | 85 | 3 |
| 0.36 | 86 | 83 | 6 |
| 1.00 | 62 | 67 | 20 |
| Example B (Solid-State) | | | |
| 0.10 | 94 | 85 | — |
| 0.16 | 83 | 81 | 6 |
| 0.22 | 79 | 76 | 9 |
| 0.30 | 59 | 68 | 18 |
| 0.45 | 54 | 63 | 22 |

[1]Temperature at 630° C. Diluent ratio from 13/1 to 19/1

TABLE II o-Ethylaniline to Indole[1]

| Time Hours | Conversion mole % | Selectivity Indole mole % | Selectivity Indolene mole % |
|---|---|---|---|
| Example 4 (Aqueous-Organic) | | | |
| 48 | 100 | 92 | 1 |
| 55 | 100 | 91 | 1 |
| 62 | 100 | 92 | 1 |
| 68 | 99 | 90 | 1 |
| Example B (Solid State) | | | |
| 50 | 97 | 85 | 1 |

[1]Temperature at 630° C. WHSV of 0.08 hr$^{-1}$

EXAMPLE 6

Cu(NO$_3$)$_2$-5H$_2$O (232.7 g, 1.00 mol) dissolved in 200 mL warm deionized water, alumina sol (2218.4 g of a 6.89% Al$_2$O$_3$ sol, by weight, 1.50 mol) and boric acid (124.1 g, 2.01 mol) dissolved in 600 mL warm deionized water were placed into a large Waring blender. After blending for several minutes a thin gel formed having a pH of 3.3. A total of 1800 mL of a solution of 20% concentrated NH$_4$OH in methanol was added to the mixture. Subsequent blending results in a thick gel having a pH of 7.5. The material was placed on four 35×45 cm trays and allowed to air dry and subsequently dried in a vacuum oven at 0.3 atm and 120° C. for 17 hours in flowing nitrogen. Several batches were calcined with the following program:

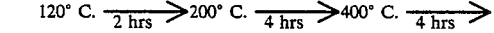
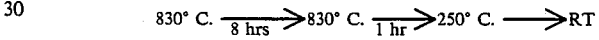

This preparation was repeated several times to obtain 143.6 g of product which was crushed and sieved to yield 20–35 mesh catalyst samples, identified as Example 6. The untreated catalyst had a BET surface area of 14 m$^2$/g, an ICP analysis of 19.8% copper, 7.4% boron, 22.6% aluminum, no detectable carbon, 0.06% hydrogen, 0.05% chlorine, and no detectable potassium.

EXAMPLE 7

A 12.7 g sample of the 20–35 mesh copper aluminum borate prepared in Example 6 was impregnated with 1.27 g KCl dissolved in 75 mL deionized water by an incipient wetness method as follows: The KCl solution was added dropwise until an even wetness appeared. The material was allowed to dry overnight. The process was repeated 3 more times, and a final 3 mL rinse of the beaker was used for a last treatment. The material was treated at 400° C. for 6 hours. The resulting material, identified as Example 7, had BET surface area of 10 m$^2$/g, an ICP analysis of 15.8% copper, 7.4% boron, 18.7% aluminum, 0.02% carbon, 0.09% hydrogen, 3.16% chlorine, and 3.07% potassium.

EXAMPLE 8

This example illustrates a comparison of the resulting catalysts of Example 6 and Example 7 for catalytic activity in oxychlorination of methane. The oxychlorination employed a fixed-bed, single-pass quartz tube flow reactor unit, 18″ long, 16-mm OD (14 mm ID) quartz tube with a 4 mm OD quartz center thermowell in a downflow mode. Heat was supplied by a 12″ long, three-zone tube furnace. The catalyst bed was supported with inert alpha-alumina (30–50 mesh) and quartz wool packing materials. A catalyst charge of 5.0 grams was centered in the heated portion of the reactor. (Typical catalyst bed lengths were 1–2 inches). A pre-blended gas feed mixture consisting of 10 mol % methane, 5 mol % oxygen, 10 mol % HCl, and 75 mol % nitrogen (prepared by Matheson) was used. The feed mixture flow was controlled by a mass flow controller. All runs were performed at 1 atm reactor pressure. Reactor effluent gas and feed gas samples were analyzed by gas chromatography using a TC detector. Nitrogen in the feed mixture was used as an internal GC standard to obtain conversion and selectivities.

Startup procedure entailed heating the catalyst charged reactor to a desired temperature and then starting a feed mixture flow, 90 mL/min measured at 1 atm and RT (corresponding to 0.071 hr$^{-1}$ methane WHSV). After 1.5–2 hours at operating conditions, a sample of reactor effluent gas was collected and GC-analyzed. Feed flow was then reduced to 60 mL/min (0.047 hr$^{-1}$ methane WHSV), and effluent was sampled after 1.5–2 hours. Feed rate was then reduced to 30 mL/min (0.024 hr$^{-1}$ methane WHSV), and effluent was sampled after 2–2.5 hours. After this sample was taken, feed was discontinued and the unit was purged with nitrogen flow overnight while raising the furnace temperature to the desired setting for the next run series.

Table III presents the results of methane oxychlorination runs with copper aluminum borate catalysts. These data illustrate that, at equivalent conversions of methane, selectivity to chloromethanes was significantly higher for potassium-containing copper aluminum borate catalyst than for comparable catalyst without potassium. Correspondingly, selectivity to carbon oxides was significantly reduced by the incorporation of potassium into the catalyst.

TABLE III

Oxychlorination of Methane

| Conditions | | Conversions | | Selectivities | |
|---|---|---|---|---|---|
| T °C. | WHSV hr$^{-1}$ | Methane mole % | Oxygen mole % | Chloro- carbons mole % | Carbon Oxides mole % |
| Example 6 (Aqueous-Organic) | | | | | |
| 400 | .071 | 8.5 | 21.9 | 73.3 | 26.7 |
| 400 | .047 | 18.6 | 38.2 | 68.2 | 31.7 |
| 400 | .024 | 22.3 | 54.8 | 63.0 | 37.0 |
| 425 | .071 | 17.6 | 38.8 | 70.1 | 30.0 |
| 425 | .047 | 15.8 | 36.0 | 66.5 | 33.5 |
| 425 | .024 | 25.4 | 63.2 | 58.5 | 41.8 |
| Example 7 (Aqueous-Organic with 10% KCl) | | | | | |
| 400 | .071 | 4.7 | 11.7 | 87.7 | 12.3 |
| 400 | .047 | 11.1 | 19.7 | 80.3 | 19.7 |
| 400 | .024 | 18.8 | 34.8 | 79.6 | 20.4 |
| 425 | .071 | 13.9 | 22.6 | 81.7 | 18.3 |
| 425 | .024 | 23.7 | 50.1 | 80.6 | 19.4 |

EXAMPLE 9

Copper nitrate hydrate (232.4 g, 1.00 mol) dissolved in 200 mL warm deionized water, alumina sol (1651.0 g of a 9.26% Al$_2$O$_3$, 1.50 mol), and boric acid (123.6 g, 2.00 mol) were placed into a 1 gallon Waring blender and mixed for 2 minutes. A total of 2 L of 20% NH$_4$OH in methanol solution was added to the mixture, in several portions, with mixing to obtain a gel which had a final pH of 8.2. The gel was air dried on tray and the vacuum dried as described above. The dry material was calcined according to the following program:

$$120° C. \xrightarrow{2 \text{ hrs}} 200° C. \xrightarrow{4 \text{ hrs}} 400° C. \xrightarrow{4 \text{ hrs}}$$

$$760° C. \xrightarrow{4 \text{ hrs}} 760° C. \xrightarrow{2 \text{ hrs}} 300° C. \xrightarrow{1 \text{ hr}}$$

$$120° C. \longrightarrow RT$$

The resulting material, identified as Example 9, had a BET surface area of 131 m$^2$/g, an ICP analysis of 21.6% copper, 28.6% aluminum, 7.4% boron, 0.06% carbon, and 0.20% hydrogen.

This material was tested for catalytic activity in the oxychlorination of methane as described above in Example 8. The oxychlorination results are shown in Table IV.

TABLE IV

Oxychlorination of Methane

| Conditions | | Conversions | | Selectivities | |
|---|---|---|---|---|---|
| T °C. | WHSV hr$^{-1}$ | Methane mole % | Oxygen mole % | Chloro- carbons mole % | Carbon Oxides mole % |
| Example 9 (Aqueous-Organic) | | | | | |
| 350 | .071 | 12.6 | 28.4 | 65.3 | 34.7 |
| 350 | .047 | 17.2 | 29.6 | 59.6 | 40.4 |

EXAMPLE 10

This example illustrates a comparison of the gels and resulting dry copper aluminum borate precursors obtained from several combinations of water and volatile organic liquids with a number of different chemical bases and copper anions.

Gels were rated visually on an intuitive scale from 1 to 4 as follows: 1 is superior; 2 is good; 3 is poor; and 4 is very poor. Dried gels were also rated visually on an intuitive scale from 1 to 4 as follows: 1 is homogeneous; 2 is some phase separation; 3 is significant phase separation; and 4 is extreme phase separation. The results are shown in Table X.

TABLE V

Comparison of Copper Aluminum Borate Precursors

| Combination[1] | | pH | | Ratings | |
|---|---|---|---|---|---|
| Base | Organic | Initial | Stored | Stored | Dried |
| NH$_4$OH | MeOH | 6.1 | 5.8 | 1 | 1 |
| NH$_4$OH | MeOH | 7.0 | 7.3 | 1 | 1 |
| NH$_4$OH | MeOH | 7.9 | 8.0 | 2 | 1 |
| NH$_4$OH | (Water) | 6.6 | 6.4 | 2 | 2 |
| NH$_4$OH | (Water) | 8.0 | 7.8 | 2 | 3 |
| NH$_4$OH | (Water) | 8.9 | 8.4 | 3 | 3 |
| TMAH | MeOH | 6.0 | 5.9 | 1 | 1 |
| TMAH | MeOH | 8.0 | 7.4 | 2 | 1 |
| TMAH | (Water) | 6.0 | 5.8 | 3 | 2 |
| TMAH | (Water) | 8.1 | 7.9 | 4 | 3 |
| NH$_4$OH | EtOH | 7.0 | 6.8 | 2 | 1 |
| NH$_4$OH | N,N DMF | 7.1 | 7.7 | 2 | 1 |
| EDA | (Water) | 7.0 | 7.5 | 3 | 4 |
| Acetate anion | | | | | |
| NH$_4$OH | (Water) | 6.0 | 6.0 | 4 | 3 |
| NH$_4$OH | (Water) | 9.0 | 8.9 | 4 | 4 |

[1]Nitrate anion except as noted
NH$_4$OH is ammonium hydroxide
TMAH is tetramethylammonium hydroxide
EDA is ethylene diamine
MeOH in methanol, EtOH is ethanol
N,N DMF is N,N-dimethylformamide
(Water) is aqueous without a volatile organic liquid

What is claimed is:

1. The process of producing copper aluminum borate which comprises forming an aqueous composition comprising a volatile organic liquid having at least partial miscibility with water, a source of copper(II) ions, a source of alumina, and a source of boria at a pH in a range from about 4 to about 10, drying the composition to form a superficially dry solid, and calcining the dry solid at a sufficiently high temperature to form crystalline copper aluminum borate.

2. The method of claim 1 wherein the volatile organic liquid consists essentially of compounds which have normal boiling points in a temperature range downward from about 140° C.

3. The method of claim 2 wherein the volatile organic liquid comprises alcohols having from about 1 to about 5 carbon atoms per molecule.

4. The method of claim 2 wherein the volatile organic liquid comprises at least one alcohol selected from the group consisting of methanol, ethanol, 2-propanol, and 2-butanol, 2-methyl2-propanol and 2-propen-1-ol.

5. The method of claim 2 wherein the volatile organic liquid comprises ethers having from about 1 to about 5 carbon atoms per molecule.

6. The method of claim 2 wherein the volatile organic liquid comprises at least one ether selected from the group consisting of methoxymethane, methoxyethane, 1-methoxypropane, 2-methoxypropane 2-ethoxypropane, 1,3-dioxane, and 1,4- dioxane.

7. The method of claim 2 wherein the volatile organic liquid comprises ketones having from about 1 to about 5 carbon atoms per molecule.

8. The method of claim 2 wherein the volatile organic liquid comprises at least one compound selected from the group consisting of propanone, butanone, 3-pentanone, 2-pentanone, and N,N-dimethylformamide.

9. The method of claim 2 wherein the dry solid is calcined to a temperature in a range from about 650° C. to about 900° C.

10. The method of claim 2 wherein the crystalline copper aluminum borate comprises $Cu_2Al_6B_4O_{17}$.

11. The process of producing copper aluminum borate which comprises forming an aqueous composition comprising a source of copper(II) ions, a source of alumina, and a source of boria, admixing with the aqueous composition a volatile organic liquid containing a chemical base, drying the composition to form a superficially dry solid, and calcining the dry solid at a sufficiently high temperature to form crystalline copper aluminum borate.

12. The method of claim 11 wherein the volatile organic liquid consists essentially of compounds which have normal boiling points in a temperature range downward from about 140° C.

13. The method of claim 12 wherein the chemical base comprises ammonium cations.

14. The method of claim 12 wherein the chemical base comprises at least one quaternary ammonium cation selected from the group consisting of tetramethylammonium, tetraethylammonium, benzyltrimethylammonium, trimethyl-n-octylammonium, dibenzyldimethylammonium, and cetyltrimethylammonium.

15. The method of claim 12 wherein the chemical base comprises ammonium hydroxide.

16. The method of claim 12 wherein the chemical base comprises tetramethylammonium hydroxide.

17. The method of claim 12 wherein the dry solid is calcined to a temperature in a range from about 650° C. to about 900° C.

18. The method of claim 12 wherein the crystalline copper aluminum borate comprises $Cu_2Al_6B_4O_{17}$.

19. The method of claim 12 wherein the volatile organic liquid comprises alcohols containing from about 1 to about 5 carbon atoms per molecule.

20. The method of claim 12 wherein the volatile organic liquid comprises at least one alcohol selected from the group consisting of methanol, ethanol, 2-propanol, 2-butanol, 2-methyl-2-propanol and 2-propen-1-ol.

21. The method of claim 12 wherein the volatile organic liquid comprises ethers having from about 1 to about 5 carbon atoms per molecule.

22. The method of claim 12 wherein the volatile organic liquid comprises at least one ether selected from the group consisting of methoxymethane, methoxyethane, 1-methoxypropane, 2-methoxypropane 2-ethoxypropane, 1,3-dioxane, and 1,4- dioxane.

23. The method of claim 12 wherein the volatile organic liquid comprises ketones having from about 1 to about 5 carbon atoms per molecule.

24. The method of claim 12 wherein the volatile organic liquid comprises at least one compound selected from the group consisting of propanone, butanone, 3-pentanone, 2-pentanone, and N,N-dimethylformamide.

25. The method of claim 19 wherein the chemical base comprises ammonium cations.

26. The method of claim 19 wherein the chemical base comprises at least one quaternary ammonium cation selected from the group consisting of tetramethylammonium, tetraethylammonium, benzyltrimethylammonium, trimethyl-n-octylammonium, dibenzyldimethylammonium, and cetyltrimethylammonium.

27. The method of claim 19 wherein the dry solid is calcined to a temperature in a range from about 650° C. to about 900° C.

28. The method of claim 19 wherein the crystalline copper aluminum borate comprises $Cu_2Al_6B_4O_{17}$.

29. The method of claim 19 wherein the chemical base comprises ammonium hydroxide.

30. The method of claim 19 wherein the chemical base comprises tetramethylammonium hydroxide.

31. The process of producing copper aluminum borate precursor which comprises forming an aqueous composition comprising a volatile organic liquid having at least partial miscibility with water, a source of copper(II) ions, a source of alumina, and a source of boria at a pH in a range from about 6 to about 10, to form a homogeneous gel which when dried to a superficially dry solid and calcined at a sufficiently high temperature forms crystalline copper aluminum borate.

* * * * *